US009126201B2

(12) United States Patent
Chen et al.

(10) Patent No.: US 9,126,201 B2
(45) Date of Patent: Sep. 8, 2015

(54) METHODS AND APPARATUSES FOR CONVECTIVE POLYMERASE CHAIN REACTION (PCR)

(75) Inventors: Pei-Jer Chen, Taipei (TW); Ping-Hei Chen, Taipei (TW); Wen-Pin Chou, Taipei (TW); Yi-Fan Hsieh, Banciao (TW); Shiou-Hwei Yeh, Sanchong (TW)

(73) Assignee: MEDIGEN BIOTECHNOLOGY CORP., Taipei (TW)

( * ) Notice: Subject to any disclaimer, the term of this patent is extended or adjusted under 35 U.S.C. 154(b) by 2 days.

(21) Appl. No.: 13/464,059

(22) Filed: May 4, 2012

(65) Prior Publication Data

US 2012/0309083 A1 Dec. 6, 2012

Related U.S. Application Data (62) Division of application No. 12/359,835, filed on Jan. 26, 2009, now Pat. No. 8,187,813.

(60) Provisional application No. 61/023,219, filed on Jan. 24, 2008.

(51) Int. Cl.
*C12Q 1/68* (2006.01)
*B01L 7/00* (2006.01)
*B01L 7/02* (2006.01)

(52) U.S. Cl.
CPC ............. *B01L 7/525* (2013.01); *C12Q 1/686* (2013.01); *B01L 7/02* (2013.01); *B01L 7/54* (2013.01); *B01L 2300/0838* (2013.01); *B01L 2300/1838* (2013.01); *B01L 2400/0472* (2013.01)

(58) Field of Classification Search
None
See application file for complete search history.

(56) References Cited

U.S. PATENT DOCUMENTS

| 6,586,233 | B2 | 7/2003 | Benett et al. |
| 2004/0152122 | A1 | 8/2004 | Hwang et al. |
| 2005/0074782 | A1 | 4/2005 | Krishnan |
| 2006/0246067 | A1 | 11/2006 | Fraser |
| 2008/0182239 | A1 | 7/2008 | Mullinax et al. |

FOREIGN PATENT DOCUMENTS

| EP | 1 712 618 A1 | 10/2006 |
| WO | WO 0104600 A1 * | 1/2001 |

OTHER PUBLICATIONS

Braun et al, "PCR by Thermal Convection," Modern Physics Letters B, vol. 18, No. 16 (2004) pp. 775-784.
Krishnan et al, "PCR in a Rayleigh-Benard Convection Cell," Science, vol. 298, p. 793, Oct. 25, 2002.
Da-Jeng Yao et al.; "Optimal Design of Micro Rayleigh-Benard Convection Polymerase Chain Reaction System"; MEMS 2006; Jan. 2006; Istanbul, Turkey; pp. 22-26.
Martin Hennig et al.; "Convective polymerase chain reaction around micro immersion heater"; Applied Physics Letters; 2005; vol. 87 (18); pp. 183901-1-183901-3.
Michael A. Innis et al.; "Optimization of PCRs"; PCR Protocols: A guide to methods and applications; Jan. 1, 1990; pp. 3-12.

* cited by examiner

*Primary Examiner* — Samuel Woolwine
(74) *Attorney, Agent, or Firm* — Birch, Stewart, Kolasch & Birch, LLP (57) ABSTRACT The present invention provides a method and apparatus for amplifying a nucleic acid sequence by polymerase chain reaction (PCR). The method comprises placing a PCR sample in a container which is heated by only a single heat source that provides a high temperature for denaturation in the bottom of the PCR sample, while annealing and extension automatically occur in different regions of the PCR sample due to the convection induced by a temperature gradient descending from the bottom of the PCR sample to the surface of the PCR sample.

17 Claims, 7 Drawing Sheets

METHODS AND APPARATUSES FOR CONVECTIVE POLYMERASE CHAIN REACTION (PCR)

CROSS-REFERENCE TO RELATED APPLICATIONS

This application is a Divisional of U.S. application Ser. No. 12/359,835 filed Jan. 26, 2009 now U.S. Pat. No. 8,187,813. This application also claims priority to U.S. Provisional Application No. 61/023,219 filed on Jan. 24, 2008. All of the above applications are hereby expressly incorporated by reference into the present application.

FIELD OF THE INVENTION

The present invention pertains to the field of amplifying nucleic acid sequences by polymerase chain reaction (PCR). More specifically, the present invention relates to convective PCR methods and apparatuses thereof.

BACKGROUND OF THE INVENTION

Amplification of specific nucleic acid sequences via polymerase chain reaction (PCR) is a mature technique and a powerful tool in medical and biological researching. Three major steps, "denaturation," "annealing" and "extension," each requiring different reaction temperatures, are necessary in this biochemical process. In today's commercialized PCR amplification technology, a sample is prepared to contain a template DNA to be amplified, a pair of oligonucleotide primers complementary to a specific sequence of each single strand of the template DNA, a thermostable DNA polymerase, and deoxynucleotide triphosphates (dNTP). A specific portion of the nucleic acid sequence of the template DNA is then amplified by repeatedly heating and cooling the sample so that the sample is cycled through three different temperatures.

The first step in PCR is the denaturation step, in which the sample is heated to a high temperature so that the double-stranded template DNA is separated into single-stranded DNAs. The second step is the annealing step, in which the sample is cooled to a lower temperature so that the primers can bind to the single-stranded DNAs formed in the first step, forming DNA-primer complexes. The last step is the polymerization (extension) step, in which the sample is maintained at a suitable temperature and the primers in the DNA-primer complexes are extended by the action of the DNA polymerase, thereby generating new single-stranded DNAs that are complementary to each strand of the template DNA. In each cycle consisting of the above three steps, the DNA sequences between the binding sites of the two primers are replicated. Typically, millions of the target nucleic acid sequence copies can be produced by repeating the PCR cycle which comprises the three steps of denaturation, annealing and extension, at different temperatures respectively for about 20 to 40 times.

The temperature of the denaturation step typically ranges from 90 to 94° C. The temperature of the annealing step is selected according to the melting temperatures ($T_m$) of the primers used, which typically ranges from 35 to 65° C. The typical temperature for the polymerization step is 72° C., since the most frequently used DNA polymerase, Taq DNA polymerase (a thermostable DNA polymerase extracted from *Thermus aquaticus*), has optimal activity at that temperature.

Since Taq DNA polymerase has a broad range of temperature, a two-step temperature cycle can also be used, in which the polymerization temperature is almost the same as the annealing temperature.

In a conventional commercial PCR machine (i.e., a thermocycler), the temperature of the sample is controlled by a thermal conduction. Briefly, a reaction vessel containing the PCR sample is made in contact with a solid metal block having a high thermal conductivity. The metal block is connected to heating and cooling devices so that its temperature can be changed to achieve desired temperatures. The conventional PCR machine adopting such method often uses a gold-plated silver block that has very high thermal conductivity and/or the Peltier cooling method in order to achieve rapid temperature changes. However, conventional PCR thermal cycling is an inefficient process because it requires the heating and cooling of material other than the PCR sample itself, which takes additional time and energy. In addition, thermocyclers are generally expensive due to the delicate nature of the machine.

Convective PCR methods were developed to perform PCR on an apparatus with two temperature-controlled devices (Krishnan, M. et al., 2002, *Science* 298: 793). Benett et al., disclosed the methods and apparatuses for convective PCR (CPCR), wherein the convectively-driven sample solution circulates in a sealed O-shaped chamber heated at one side in U.S. Pat. No. 6,586,233, issued on Jul. 1, 2003. Hwang et al. disclosed the methods and apparatuses for convective PCR, wherein multiple heat sources are used to maintain different temperature zones in the sample solution so that the three steps of PCR occur sequentially and repeatedly while the sample cycles between each zone in U.S. patent application Ser. No. 10/801,342, published on Mar. 15, 2004 under US Publication No. 2004/0152122.

Although some methods have been provided for a convective PCR, for which the apparatuses were involved complicated structures, and were expensive, therefore hindering their commercial application. There is still a need for a more convenient and practical method and apparatus for a convective PCR (CPCR).

BRIEF SUMMARY OF THE INVENTION

The present invention provides a novel method and apparatus for conveniently, efficiently and economically performing convective PCR (CPCR).

Accordingly, in a first aspect, the present invention provides a method for amplifying a target nucleic acid sequence via polymerase chain reaction (PCR), comprising the steps of:
 (1) providing a tube-like container;
 (2) placing a PCR sample in a tube-like container, wherein the PCR sample contains a template DNA having the target nucleic acid sequence to be amplified, deoxyribonucleic acid (DNA) polymerases, deoxyadenosine triphosphates (dATPs), deoxycytidine triphosphates (dCTPs), deoxyguanosine triphosphates (dGTPs), deoxythymidine triphosphates (dTTPs), and at least two oligonucleotide primers having a sequence complementary to the 3' end of the target nucleic acid sequence wherein the primers are designed to have a melting temperature ($T_m$) between about 40° C. to about 90° C.;
 (3) embedding the bottom part of the container in a heat source, and then heating the PCR sample to allow the primers melt and maintaining a steady temperature in ° C. of the surface of the PCR sample (Ts) less than the temperature in ° C. of the melting temperature of the primers ($T_m$) by at least about 2° C. so that a temperature gradient descending from the bottom to the top of the PCR sample is resulted, which induces a convection and makes the following events occur sequentially and repeatedly within different regions of the sample: (i) denaturation, in which the double-stranded template DNA separates into two single-stranded DNAs, (ii) annealing, in which the primers hybridize to the single-stranded DNAs, forming DNA-primer complexes, and (iii) polymerization (extension), in which the primers in the DNA-primer complexes are extended by the DNA polymerase.

In a second aspect, the present invention provides an apparatus for performing a nucleic acid sequence amplification by polymerase chain reaction (PCR) through the method of the present invention, comprising (i) a single heat source; and (ii) one or more tube-like containers in which the PCR is performing; and (iii) a holder with a means for homogenizing the heat accumulated by in multiple containers.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings some embodiments, which are presently preferred. It should be understood, however, that the invention is not limited to the precise arrangements and instrumentalities shown.

In the drawings:

FIGS. 1A and 1B are the sketch of an ideal single circular convective flow of a CPCR according the present invention, wherein the axis of X represents a time scale, and the axis of Y represents a temperature scale, 10, 20 and 30 means the ranges of the temperatures for the three events occurring in a PCR including denaturation, annealing and extension, respectively; and wherein FIG. 1A shows the temperature changes of a PCR sample in a CPCR according to the present invention, and FIG. 1B shows the temperature changes of a PCR sample in a conventional PCR as comparison.

FIGS. 5A, 5B and 5C show the CPCR results of Example 3 using the CPRC method according to the invention by the apparatuses with and without heat homogenizers; wherein

DETAILED DESCRIPTION OF THE INVENTION

The present invention provides a novel method and apparatus for performing a convective PCR.

One embodiment of the present invention is a method for amplifying a target nucleic acid sequence by PCR, comprising the steps of:

(1) providing a tube-like container;

(2) placing a PCR sample in a tube-like container, wherein the PCR sample contains a template DNA having the target nucleic acid sequence to be amplified, DNA polymerases, deoxyadenosine triphosphates (dATPs), deoxycytidine triphosphates (dCTPs), deoxyguanosine triphosphates (dGTPs), deoxythymidine triphosphates (dTTPs), and at least two oligonucleotide primers having a sequence complementary to the 3' end of the target nucleic acid sequence wherein the primers are designed to have a melting temperature ($T_m$) between about 40° C. to about 90° C.;

(3) embedding the bottom part of the container in a heat source, and then heating the PCR sample to allow the primers melt and maintaining a steady temperature in ° C. of the surface of the PCR sample (Ts) less than the temperature in ° C. of the melting temperature of the primers ($T_m$) by at least about 2° C. so that a temperature gradient descending from the bottom to the top of the PCR sample is resulted, which induces a convection and makes the following events occur sequentially and repeatedly in different regions of the sample: (i) denaturation, in which the double-stranded template DNA separates into two single-stranded DNAs, (ii) annealing, in which the primers hybridize to the single-stranded DNAs, forming DNA-primer complexes, and (iii) polymerization, in which the primers in the DNA-primer complexes are extended by the DNA polymerase.

Figure 1A:
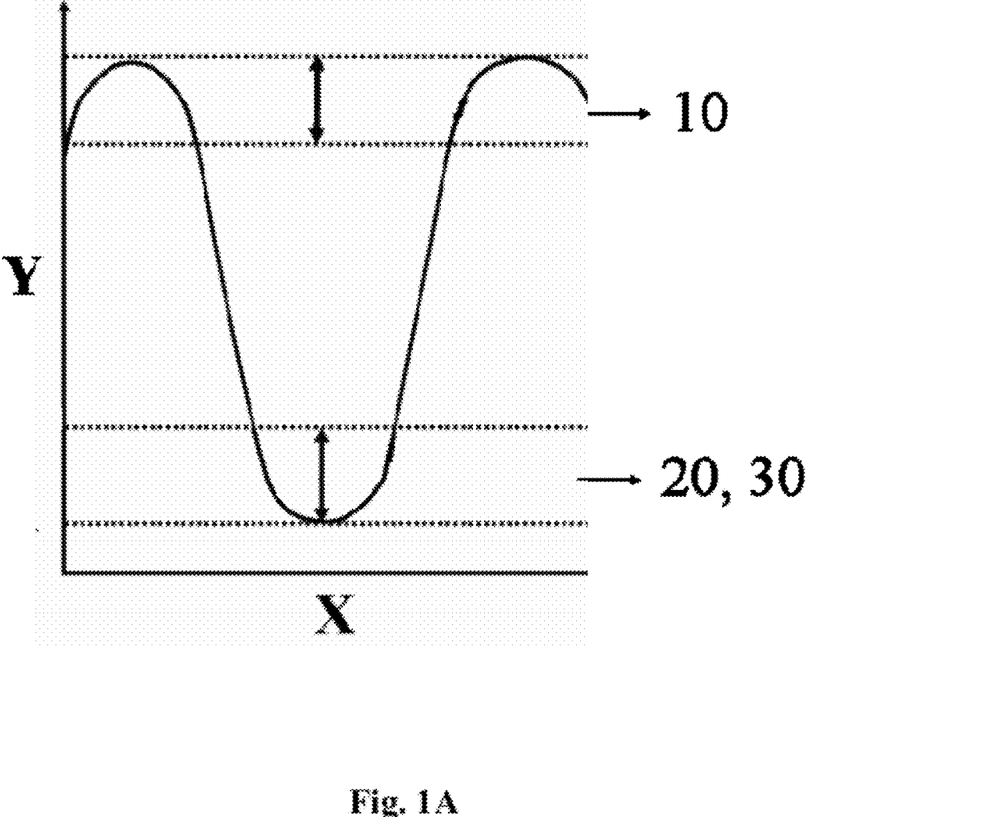
Figure 1B:
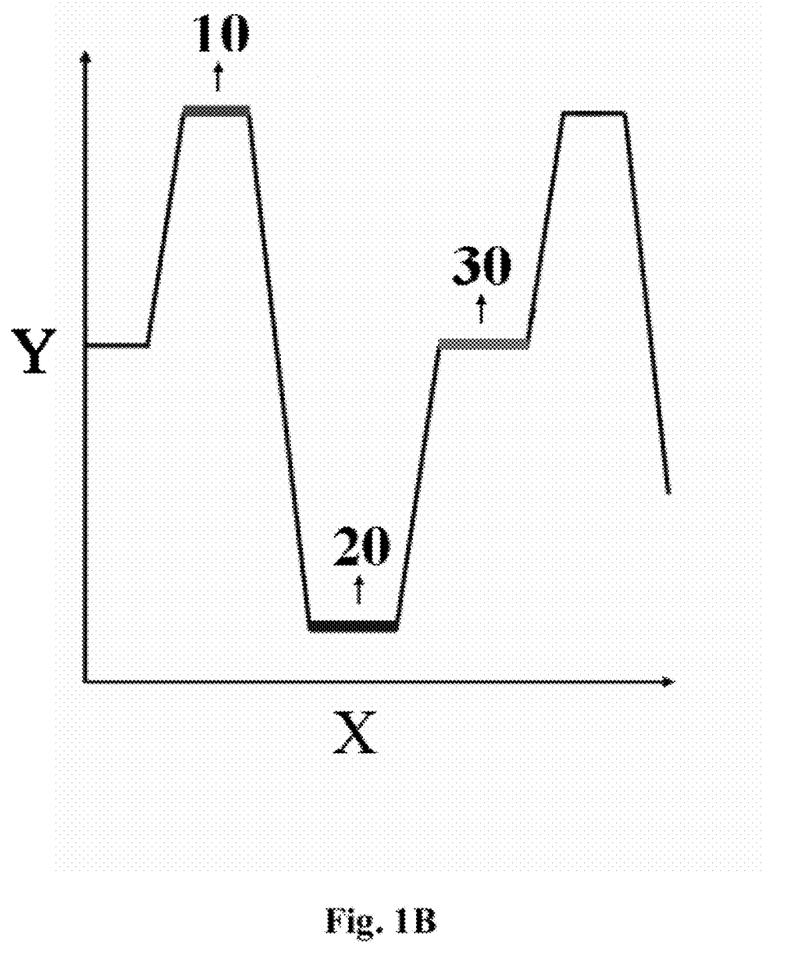

To perform the convective PCR (CPCR) of the present invention, the random and chaotic natural convection in a PCR sample must be converted into a steady single convection cycle so that template DNA can be amplified step-by-step while cycling at different temperatures required for the different events. As shown in FIGS. 1A and 1B, there are three events occurring in a PCR: (i) denaturation at a high temperature by heating, (ii) annealing and (iii) extension (polymerization) at the temperatures lower than the temperature for denaturation. Specially, in a convective PCR, the low temperature should be maintained for a sufficient time for performing the annealing of the PCR sample.

It was unexpectedly found in the present invention that when a steady temperature in ° C. of the surface of the PCR sample (Ts) is kept at a temperature less than the temperature in ° C. of the melting temperature of the primers ($T_m$) by at least about 2° C., a temperature gradient descending from the bottom to the top of the PCR sample is resulted, which induces a convection and makes the events occur sequentially and repeatedly in the different regions of the PCR sample, which was illustrated in Example 2.

In the method of the present invention, the tube-like container may be sealed with an oil to avoid evaporation of the sample during the reaction. In an embodiment of the present invention, the oil may be a mineral oil. According to the invention, a drop of mineral oil may be added on the top of the PCR sample so that the surface of the sample is covered by the oil.

To perform the convective PCR of the present invention, a temperature gradient descending from the bottom to the top of the PCR sample must be maintained. This is achieved by heating the bottom part of the tube-like container, while maintaining a steady temperature in ° C. of the surface of the PCR sample (Ts) less than the temperature in ° C. of the melting temperature of the primers ($T_m$) by at least about 2° C. This can be achieved by designing appropriate primers having a given melting temperature and controlling the parameters of the PCR.

To achieve the single circular convective flow, a computer simulation for the CPCR according to the invention was conducted to learn the relationship between the parameters of the PCR: the viscosity in Ns/m² of the PCR solution (µ), the inner diameter in mm of the container (d), and the surface temperature in ° C. of the PCR sample (Ts), which may be determined according to the formula below:

$$V=(A \times T_s + B - 500\mu + 0.7) \times e^{(1.86 + 100\mu)d}$$

in which A is a value between −0.019 and −0.016, and B is a value between 1.85 and 2.27. In one preferred embodiment of the invention, A is a value of −0.01812, and B is a value of 2.1.

In the embodiments of the present invention as found, Ts is between about 40° C. and about 80° C.; µ is between 0.001 Ns/m² and 0.0018 Ns/m²; and d is between 0.6 mm and 5.0 mm. In a more preferred embodiment, Ts is between about 55° C. and about 70° C.; µ is between 0.001 Ns/m² and 0.0016 Ns/m²; and d is between 0.8 mm and 4.0 mm. In the most preferred embodiment, Ts is between about 65° C. and about 68° C.; µ is between 0.001 Ns/m² and 0.0014 Ns/m²; and d is between 0.8 mm and 2.5 mm.

To increase the viscosity of the PCR sample, nonreactive liquid materials may be added to the sample. Suitable materials are any nonreactive organic or inorganic materials, including but not limited to glycerol, NP-40, Tween 20, EDTA, DMSO, formamide, betain, and gelatin. Preferred materials are glycerol, NP-40, Tween 20, and EDTA. The most preferred material is glycerol. The amount of the viscosity-increasing material added should be any amount able to achieve the required viscosity. In an embodiment of the present invention, 4% to 8% v/v of glycerol is added to the PCR sample.

The present invention provides an apparatus for performing a nucleic acid sequence amplification by polymerase chain reaction (PCR) through the method of the present invention, comprising (i) a single heat source; and (ii) one or more tube-like containers in which the PCR is performing; and (iii) a means for homogenizing heat accumulated in multiple containers.

The heat source used in the present invention may be a simple heating device with a means of temperature control. Suitable heat source include but not limited to dry-bath incubators, water-bath incubators, and oil-bath incubators. In an embodiment of the present invention, the heat source is boiling water.

The tube-like containers of the present invention may be manufactured with any material, as long as the material is biocompatible and has a heat resistance of at least 120° C. Suitable materials include polymeric materials such as polypropylene (PP), polycarbonate (PC), polyethylene (PE), polysulfone (PSF) and polyether sulfone (PES), as well as glass.

In the embodiment of the invention, the means for homogenizing heat accumulated in multiple containers is a heat homogenizer, which may be made from a metal plate so that the temperatures of the multiple containers can be homogenized in a multiple-tested PCR. The term "heat homogenizer" used herein refers to an external casing usually made from aluminium or copper that is designed to cover an electronic device and dissipate heat, which is usually used for CPU (Central Processing Unit) of a computer. For instance, the apparatus for performing the multiple testing CPCR may comprise a holder equipped with heat homogenizers. In the apparatus according to the invention, the heat homogenizers are used for dissipating heat accumulated in space between the containers for a multiple-testing CPCR. In the embodiment of the invention, the holder is designed for holding multiple containers in a rectangular matrix. In one embodiment of the invention, the holder is designed for holding 96 containers arranged in a 8:12 rectangular matrix.

Figure 4:
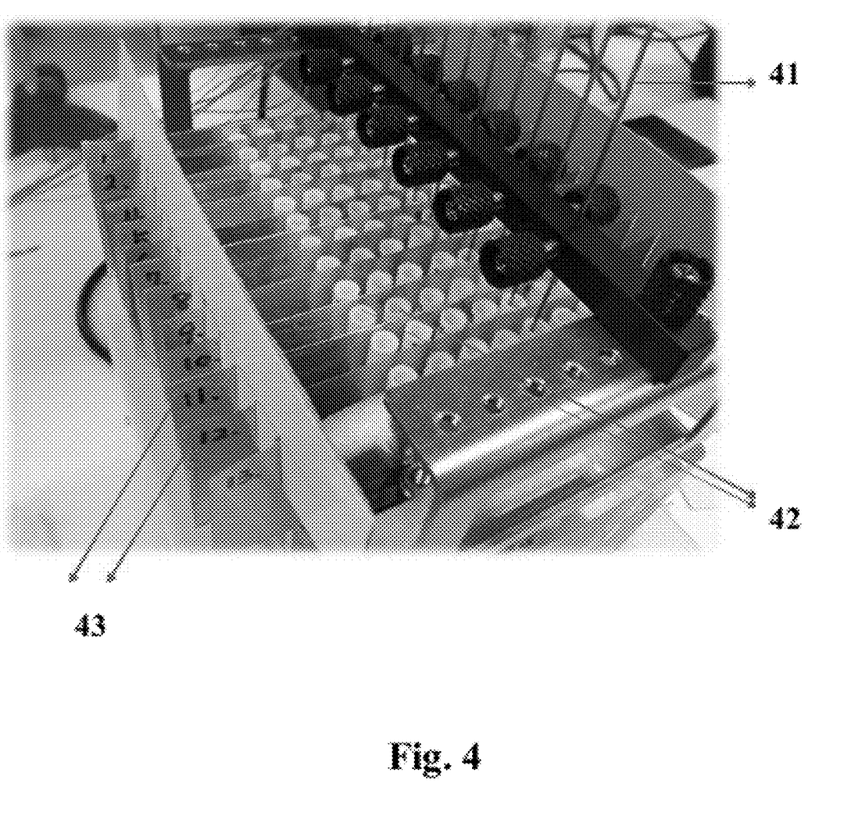
FIG. 4 is an image showing one embodiment of the apparatus with heat homogenizers according to the invention.

The apparatus of the present invention may also comprise a means for measuring the temperature at the surface of the PCR sample. An example of such a means is a thermometer 41.

The present invention is further illustrated with the following examples. These examples are offered for the purpose of illustration and are not to be construed in any way as limiting the scope of the present invention.

EXAMPLES

In the examples below, the following abbreviations have the following meanings: ° C.=degree Celsius; hr=hour; min=minute; sec=second; M=molar; mM=millimolar; µM=micromolar; L or l=liter; ml=milliliter; µl=microliter; G or g=gram; mg=milligram; µg=microgram; pg=picogram. Abbreviations not defined have their generally accepted meanings.

Example 1

1. Materials and Methods 1.1 Sample

The PCR sample contained the following reagents: 3.32 pg of pHBV-48 (GenBank accession No. NC003977) inserted in pGEM®-3Z vector (Promega Corporation, Madison, Wis.) as template DNA, 1.5 pmol of primer F118 (5'-CCTAGCAGCT-TGTTTTGCTCGCAGCCG-3') (SEQ ID NO: 3), 1.5 pmol of primer R145 (5'-TCCAGTTGGCAGCACAGCCTAG-CAGC-3') (SEQ ID NO: 4), 7.5 µl of LightCycler® FastStart DNA Master HybProbe hot start reaction mix (Rosche Applied Science, Indianapolis, Ind.), and 5% v/v of glycerol.

A computer simulation for simulate the abstract model of the CPRC according to the invention was conducted, and the formula for the parameters was obtained and given below:

$$V=(A \times T_s + B - 500\mu + 0.7) \times e^{(1.86 + 100\mu)d}$$

wherein A=−0.01812, B=2.1, Ts=68° C., µ=0.0012 Ns/m2, and d=2.2 mm.

Based on the formula, the total volume of the PCR sample being 75.44 could be calculated.

1.2 Apparatus

The apparatus for performing the convective PCR according to the invention was composed of the following elements: a heating tank with temperature-control function; multiple glass capillaries (inner diameter=2.2 mm) as reaction containers 42; and a holder with heat homogenizers 43, as shown in FIG. 4.

1.3 Procedure

The temperature of the silicon oil in the heating tank was maintained at 95° C. throughout the experiment. The PCR sample and a negative control (same ingredients as the sample, except that the template DNA was substituted with ddH$_2$O of the same volume, 30λ) were individually injected into a glass capillary, and sealed with 10 µl of mineral oil. The capillaries were then put on the stand of the heating tank so that the bottom part of each of the capillaries was embedded in the heated silicon oil for 25 mins. During the whole time of reaction, ambient temperature was maintained at room temperature. When time was up, the capillaries were removed from the stand and 2 µl of the resultant mixture in each of the capillaries was taken for electrophoretic analysis.

2. Results

Figure 2:
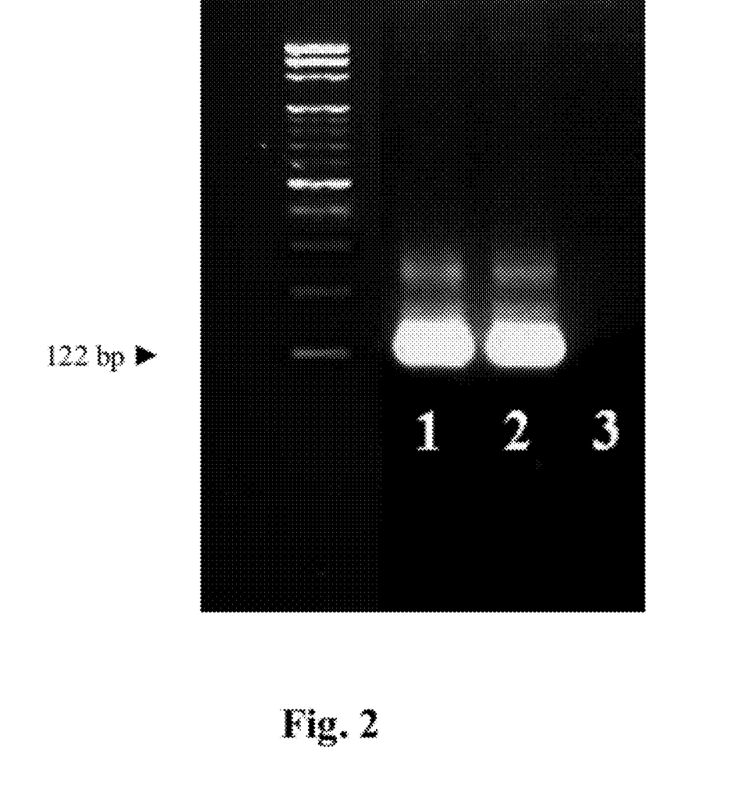
FIG. 2 is an image showing the PCR results of Example 1, wherein lanes 1 and 2 represent the results of two repetitive experiments using the same sample and protocol, while lane 3 represents the result of a negative control.

The resulted PCR reaction products were analyzed on 2% agarose gel, and the results are presented in FIG. 2. As shown in FIG. 2, the bright bands in lanes 1 and 2 show that the convective PCR method of the present invention has correctly amplified the 122-bp target sequence in less than half an hour. When using a conventional thermocycler, the whole reaction would take more than one and a half hours, and still resulted in fewer copies of products (data not shown). Therefore, the method of the present invention is superior to the conventional PCR method in view of its efficiency and economy.

Example 2

Seven primer pairs were designed to have a melting temperature (T$_m$) ranging from 58° C.~80° C. as shown in Table 1, wherein the value of T$_m$ of each primer was calculated using the Program Lightcycler Probe Design 2.0 (Roche, Germany).

Figure 3:
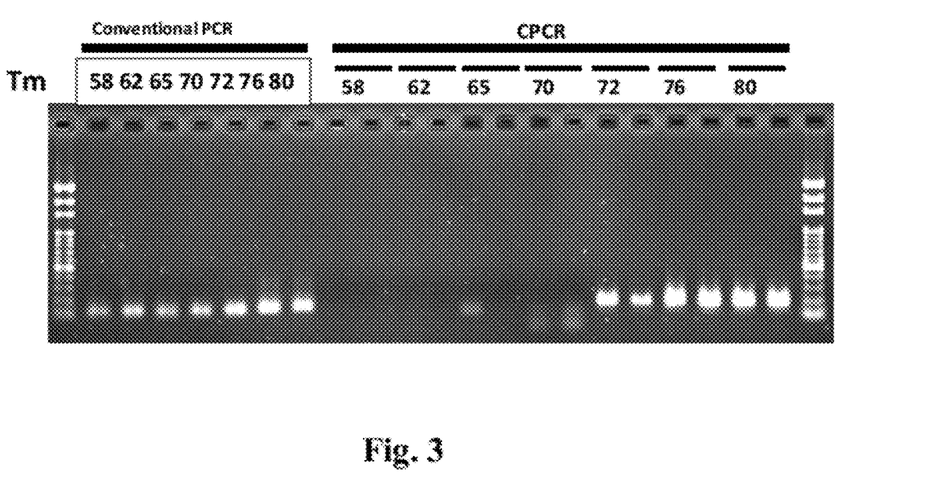
FIG. 3 is an image showing the PCR results of Example 2, wherein each of the lanes remarked as "CPCR" is the result of the PCR sample by the method according to the present invention using the primer pair having a melting temperature ($T_m$) as the number indicated in the top of each lane, at the temperature of the surface of the PCR sample being 68° C.; and each of the lanes remarked as "Conventional PCR" is the result of the same sample by the method of a conventional PCR as comparison.

A CPCR was performed using each pair of the primers as shown in Table 1 a temperature of the PCR sample (Ts) being 68° C. according to the method and protocol stated in Example 1. The CPCR results were shown in FIG. 3, wherein the 122-bp band was found when the primer having a T$_m$ being 70 or more than 70 w used. Given the finding, it was concluded that a CPCR could be successfully performed when the Ts value s less than the T$_m$ value by at least about 2° C.

TABLE 1

Sequences as designed primers and Tm values

| Name | mer | Tm (° C.) | 5'- | SEQ ID |
|---|---|---|---|---|
| HBV set 1-F | 35 | 80 | GCGGAACTCCTAGCAGCTTGTTTTGCTCGCAGCCG | 1 |
| HBV set 1-R | 33 | 80 | CGCAGGATCCAGTTGGCAGCACAGCCTAGCAGC | 2 |
| HBV set 2-F | 27 | 77 | CCTA GCAG CTTG TTTT GCTC GCAG CCG | 3 |
| HBV set 2-R | 26 | 76 | TCCA GTTG GCAG CACA GCCT AGCA GC | 4 |
| HBV set 3-F | 23 | 73 | GCAGCTTGTTTTGCTCGCAGCCG | 5 |
| HBV set 3-R | 22 | 72 | GTTGGCAGCACAGCCTAGCAGC | 6 |
| HBV set 4-F | 20 | 70 | GCTTGTTTTGCTCGCAGCCG | 7 |
| HBV set 4-R | 19 | 70 | GGCAGCACAGCCTAGCAGC | 8 |
| HBV set 5-F | 18 | 65 | TTGTTTTGCTCGCAGCCG | 9 |
| HBV set 5-R | 17 | 65 | CAGCACAGCCTAGCAGC | 10 |
| HBV set 6-F | 15 | 62 | TTTTGCTCGCAGCCG | 11 |
| HBV set 6-R | 15 | 62 | GCACAGCCTAGCAGC | 12 |
| HBV set 7-F | 13 | 61 | TTGCTCGCAGCCG | 13 |
| HBV set 7-R | 14 | 58 | CACAGCCTAGCAGC | 14 |

Example 3

Figure 5A:
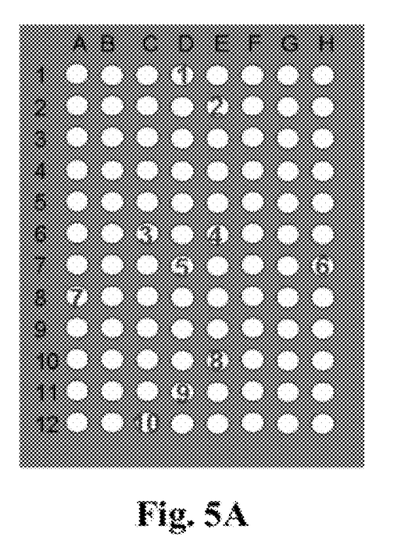
FIG. 5A shows the numbering of the positions of the samples.
Figure 5B:
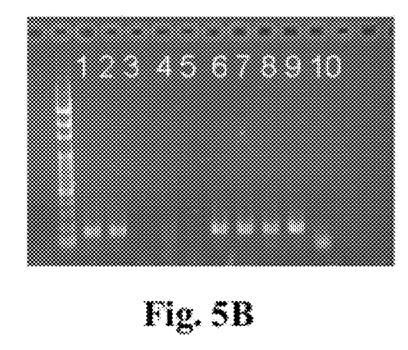
FIG. 5B shows the CPCR results by the apparatus without heat homogenizers.
Figure 5C:
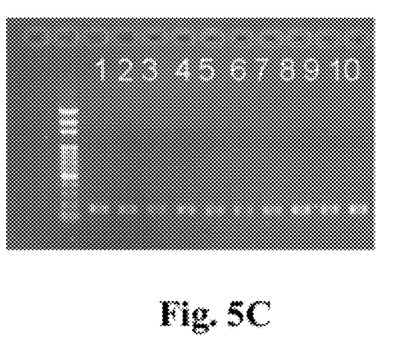
FIG. 5C shows the CPCR results by the apparatus with heat homogenizers.

A CPCR using each of the apparatuses with and without a holder with heat homogenizers was performed. The holder was designed for holding 96 containers arranged in a 8 (columns A-H): 12 (lines 1-12) rectangular matrix, see FIG. 4. Ten samples at 10 different positions in this matrix were selected and numbered as indicated in FIG. 5A. The CPCR results were given in FIG. 5B (without heat homogenizers) and 5C (with heat homogenizers). It was shown in FIGS. 5B and 5C that no results were found in the positions 3, 4 and 5 that were around the center of the matrix when the apparatus without heat homogenizers was used; however, while the CPCR results were good in all the positions when the apparatus with heat homogenizers were used.

Figure 6:
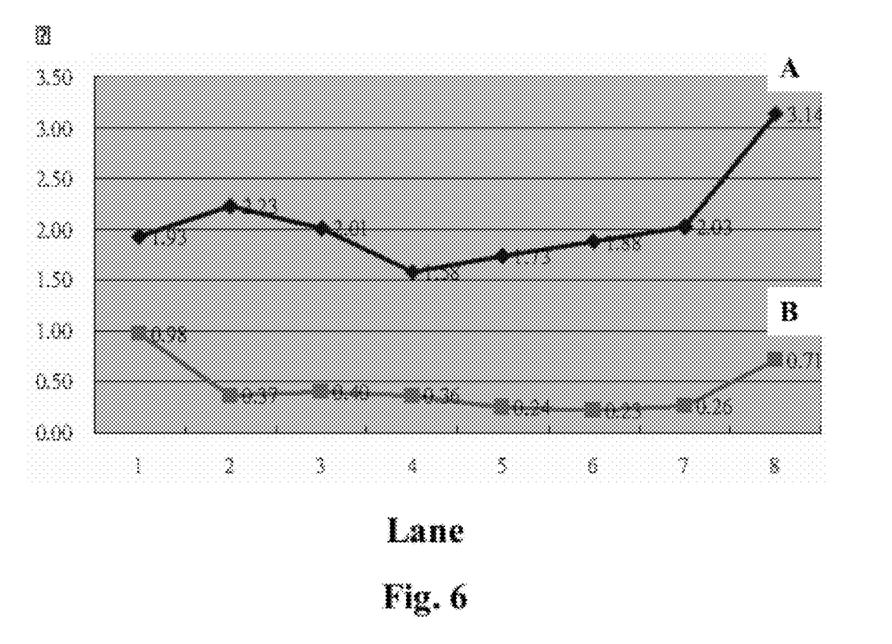
FIG. 6 shows the variations of the surface temperatures (Ts) of the PCR sample of each of the samples numbered 1-8 as shown in FIG. 5A, by the CPCR method according to the invention for two groups using the apparatus with and without heat homogenizers, wherein the curve A (-♦-) represents the variations of the group using the apparatus without heat homogenizers and the curve B (-■-) represents the variations of the group using the apparatus with heat homogenizers.

A further comparison between the apparatuses with and without heat homogenizers was shown in FIG. 6. The surface temperature (Ts) of each of the PCR samples numbered as 1-10 was measured and recorded during 30-minutes after heating; and the variation of the surface temperature (Ts) for each sample during 30 minutes was shown in FIG. 6, wherein the curve A represented the variations of the group using the apparatus without heat homogenizers, and the curve B represents the variations of the group using the apparatus with heat homogenizers. It was indicated that the variations of the Ti values for the group using the apparatus with heat homogenizers were in 1° C.; however, the variations of the group using the apparatus without heat homogenizers were in 2~3°

C. It suggested that the apparatus with heat homogenizers provide a steady surface temperature for each position in one experiment, and a stable thermal condition for the CPCR.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An apparatus for performing a method of a nucleic acid sequence amplification by polymerase chain reaction (PCR), which apparatus comprising:
   (i) a single heat source;
   (ii) multiple tube-like containers for loading a PCR sample, and
   (iii) a holder for holding the multiple tube-like containers,
   wherein the containers are disposed to be in thermal contact with the single heat source, with a bottom part of each of the containers embedded in the single heat source, to provide a relatively high temperature at a bottom part of the PCR sample, and in such a manner that air surrounds the containers above the bottom part of each of the containers to remove heat to lead to a relatively low temperature on a top surface of the PCR sample, whereby a temperature gradient descending from the bottom to the top is resulted in the PCR sample, which induces a convection and makes three events, (i) denaturation, (ii) annealing and (iii) extension, occur sequentially and repeatedly in different regions of the PCR sample;
   wherein the apparatus does not include a thermally conductive block in contact with an upper part of the each of the containers to remove heat from the PCR sample; and
   wherein said holder is equipped with a means which is disposed without contact with the containers for dissipating heat accumulating in the air surrounding the containers above the bottom part of each of the containers.

2. The apparatus according to claim 1, wherein the means is made from aluminum or copper.

3. The apparatus according to claim 1, wherein the means is a metal plate.

4. The apparatus according to claim 1, wherein the single heat source is selected from the group consisting of a dry-bath incubator, a water-bath incubator, and an oil bath incubator.

5. The apparatus according to claim 1, wherein the single heat source is a dry-bath incubator.

6. The apparatus according to claim 1, wherein the single heat source is a water-bath incubator.

7. The apparatus according to claim 1, wherein the surface temperature of the PCR sample is between 40° C. to 80° C.

8. The apparatus according to claim 1, wherein the surface temperature of the PCR sample is between 55° C. to 70° C.

9. The apparatus according to claim 1, wherein the surface temperature of the PCR sample is between 65° C. to 68° C.

10. The apparatus according to claim 1, wherein the means comprises a plurality of metal plates.

11. The apparatus according to claim 10, wherein the metal plates are parallel disposed in a space around the containers above the bottom part of each of the containers.

12. The apparatus according to claim 10, wherein the metal plates and the containers are alternately disposed.

13. An apparatus for performing a method of a nucleic acid sequence amplification by polymerase chain reaction (PCR), which apparatus consisting of:
   (i) a single heat source;
   (ii) multiple tube-like containers for loading a PCR sample, and
   (iii) a holder for holding the multiple tube-like containers,
   wherein the containers are disposed to be in thermal contact with the single heat source, with a bottom part of each of the containers embedded in the single heat source, to provide a relatively high temperature at a bottom part of the PCR sample, and in such a manner that air surrounds the containers above the bottom part of each of the containers to remove heat to lead to a relatively low temperature on a top surface of the PCR sample, whereby a temperature gradient descending from the bottom to the top is resulted in the PCR sample, which induces a convection and makes three events, (i) denaturation, (ii) annealing and (iii) extension, occur sequentially and repeatedly in different regions of the PCR sample; and
   wherein the holder is equipped with a means which is disposed without contact with the containers for dissipating heat accumulating in the air surrounding the containers above the bottom part of each of the containers.

14. The apparatus according to claim 13, wherein the means is a plurality of metal plates.

15. The apparatus according to claim 14, wherein the metal plates are parallel disposed in a space around the containers above the bottom part of each of the containers.

16. The apparatus according to claim 14, wherein the metal plates and the containers are alternately disposed.

17. An apparatus for performing a method of a nucleic acid sequence amplification by polymerase chain reaction (PCR), which apparatus consisting of:
   (i) a single heat source;
   (ii) multiple tube-like containers for loading a PCR sample, and
   (iii) a holder for holding the multiple tube-like containers,
   wherein the containers are disposed to be in thermal contact with the single heat source, with a bottom part of each of the containers embedded in the single heat source, to provide a relatively high temperature at a bottom part of the PCR sample, and in such a manner that air surrounds the containers above the bottom part of each of the containers to remove heat to lead to a relatively low temperature on a top surface of the PCR sample, whereby a temperature gradient descending from the bottom to the top is resulted in the PCR sample, which induces a convection and makes three events, (i) denaturation, (ii) annealing and (iii) extension, occur sequentially and repeatedly in different regions of the PCR sample; and wherein the holder is equipped with a heat homogenizer, which is disposed without contact with the containers, wherein the heat homogenizer is configured to dissipate heat in the air surrounding the containers above the bottom part of each of the containers.

* * * * *

```
                            SEQUENCE LISTING

<160> NUMBER OF SEQ ID NOS: 14

<210> SEQ ID NO 1
<211> LENGTH: 35
<212> TYPE: DNA
<213> ORGANISM: Artificial Sequence
<220> FEATURE:
<223> OTHER INFORMATION: HBV set 1-F

<400> SEQUENCE: 1
gcggaactcc tagcagcttg ttttgctcgc agccg                              35

<210> SEQ ID NO 2
<211> LENGTH: 33
<212> TYPE: DNA
<213> ORGANISM: Artificial Sequence
<220> FEATURE:
<223> OTHER INFORMATION: HBV set 1-R

<400> SEQUENCE: 2
cgcaggatcc agttggcagc acagcctagc agc                               33

<210> SEQ ID NO 3
<211> LENGTH: 27
<212> TYPE: DNA
<213> ORGANISM: Artificial Sequence
<220> FEATURE:
<223> OTHER INFORMATION: HBV set 2-F

<400> SEQUENCE: 3
cctagcagct tgttttgctc gcagccg                                      27

<210> SEQ ID NO 4
<211> LENGTH: 26
<212> TYPE: DNA
<213> ORGANISM: Artificial Sequence
<220> FEATURE:
<223> OTHER INFORMATION: HBV set 2-R

<400> SEQUENCE: 4
tccagttggc agcacagcct agcagc                                       26

<210> SEQ ID NO 5
<211> LENGTH: 23
<212> TYPE: DNA
<213> ORGANISM: Artificial Sequence
<220> FEATURE:
<223> OTHER INFORMATION: HBV set 3-F

<400> SEQUENCE: 5
gcagcttgtt ttgctcgcag ccg                                          23

<210> SEQ ID NO 6
<211> LENGTH: 22
<212> TYPE: DNA
<213> ORGANISM: Artificial Sequence
<220> FEATURE:
<223> OTHER INFORMATION: HBV set 3-R

<400> SEQUENCE: 6
```

-continued

```
gttggcagca cagcctagca gc                                              22

<210> SEQ ID NO 7
<211> LENGTH: 20
<212> TYPE: DNA
<213> ORGANISM: Artificial Sequence
<220> FEATURE:
<223> OTHER INFORMATION: HBV set 4-F

<400> SEQUENCE: 7
gcttgttttg ctcgcagccg                                                 20

<210> SEQ ID NO 8
<211> LENGTH: 19
<212> TYPE: DNA
<213> ORGANISM: Artificial Sequence
<220> FEATURE:
<223> OTHER INFORMATION: HBV set 4-R

<400> SEQUENCE: 8
ggcagcacag cctagcagc                                                  19

<210> SEQ ID NO 9
<211> LENGTH: 18
<212> TYPE: DNA
<213> ORGANISM: Artificial Sequence
<220> FEATURE:
<223> OTHER INFORMATION: HBV set 5-F

<400> SEQUENCE: 9
ttgttttgct cgcagccg                                                   18

<210> SEQ ID NO 10
<211> LENGTH: 17
<212> TYPE: DNA
<213> ORGANISM: Artificial Sequence
<220> FEATURE:
<223> OTHER INFORMATION: HBV set 5-R

<400> SEQUENCE: 10
cagcacagcc tagcagc                                                    17

<210> SEQ ID NO 11
<211> LENGTH: 15
<212> TYPE: DNA
<213> ORGANISM: Artificial Sequence
<220> FEATURE:
<223> OTHER INFORMATION: HBV set 6-F

<400> SEQUENCE: 11
ttttgctcgc agccg                                                      15

<210> SEQ ID NO 12
<211> LENGTH: 15
<212> TYPE: DNA
<213> ORGANISM: Artificial Sequence
<220> FEATURE:
<223> OTHER INFORMATION: HBV set 6-R

<400> SEQUENCE: 12
gcacagccta gcagc                                                      15

<210> SEQ ID NO 13
<211> LENGTH: 13
<212> TYPE: DNA
<213> ORGANISM: Artificial Sequence
```

```
<220> FEATURE:
<223> OTHER INFORMATION: HBV set 7-F

<400> SEQUENCE: 13
ttgctcgcag ccg                                                              13

<210> SEQ ID NO 14
<211> LENGTH: 14
<212> TYPE: DNA
<213> ORGANISM: Artificial Sequence
<220> FEATURE:
<223> OTHER INFORMATION: HBV set 7-R

<400> SEQUENCE: 14
cacagcctag cagc                                                             14
```